United States Patent [19]
Boucher

[11] 3,968,248
[45] July 6, 1976

[54] METHOD AND SPORICIDAL COMPOSITIONS FOR SYNERGISTIC DISINFECTION OR STERILIZATION

[75] Inventor: Raymond Marcel Gut Boucher, New York, N.Y.

[73] Assignee: Wave Energy Systems, Inc., New York, N.Y.

[22] Filed: July 16, 1975

[21] Appl. No.: 596,372

Related U.S. Application Data

[63] Continuation-in-part of Ser. No. 155,233, June 21, 1971, abandoned.

[52] U.S. Cl. ............................................. 424/333
[51] Int. Cl.² .......................................... A01N 9/24
[58] Field of Search ................................. 424/333

[56] References Cited
UNITED STATES PATENTS

| | | | |
|---|---|---|---|
| 2,801,216 | 7/1957 | Yoder et al. | 424/333 |
| 3,016,328 | 1/1962 | Pepper et al. | 424/333 |
| 3,057,775 | 10/1962 | Rendon | 424/333 |
| 3,282,775 | 11/1966 | Stonehill | 424/333 |
| 3,497,590 | 2/1970 | Elgin | 424/55 |
| 3,503,885 | 3/1970 | Wedell | 252/95 |
| 3,650,964 | 3/1972 | Sedilar | 252/106 |
| 3,666,668 | 5/1972 | Klausner | 424/329 |
| 3,697,222 | 10/1972 | Sierra | 21/58 |

FOREIGN PATENTS OR APPLICATIONS

| | | | |
|---|---|---|---|
| 865,913 | 3/1971 | Canada | 21/7 |

OTHER PUBLICATIONS

"Potentially Infectious Agents . . . Aeruginosa," Wilkoff et al., Applied Nicrobiology, Apr. 1971, pp. 647–652.

"Preservation of Toilet . . . Nonionics," Wedderburn et al., — J. of Soc. Cos. Chemists 210–228 (1958), 11-29-57.

"Potentially Infectious . . . Bed Pans", Sidewell et al., 19 (1) 53–59 (1970).

J. of Pharm. Science, 53 (10), pp. 1273–1275 (1964), Borick et al. — "Alkalinized Glutaraldehyde . . . Agent."

Currents in Mod. Biology 1, pp. 14–20 (1967) — EGYU'D — "Studies on Cell Division . . . ".

*Primary Examiner*—Albert T. Meyers
*Assistant Examiner*—D. W. Robinson
*Attorney, Agent, or Firm*—Shoemaker and Mattare, Ltd.

[57] ABSTRACT

This invention relates to a method for disinfecting or sterilizing medical, surgical, dental instruments or other objects in liquid phase with improved sporidical compositions. The method object of the invention is based upon the synergistic effects observed when combining nonionic and anionic surfactants with aqueous or alcoholic glutaraldehyde solutions. The method can be used also with ultrasonic irradiation over a wide frequency range (10 to 850 kHz). Two types of particularly effective synergistic sporicidal compositions are also described.

3 Claims, No Drawings

METHOD AND SPORICIDAL COMPOSITIONS FOR SYNERGISTIC DISINFECTION OR STERILIZATION

CROSS REFERENCE TO RELATED APPLICATION

This application is a continuation-in-part application of copending application Ser. No. 155,233, filed June 21, 1971, now abandoned entitled "Method and Sporicidal Compositions for Synergistic Disinfection or Sterilization."

BACKGROUND OF THE INVENTION

This invention relates to a method for disinfecting or sterilizing objects in liquid phase with improved chemosterilizer compositions. The method object of our invention is based upon the synergistic sporicidal effects observed when using relatively moderate temperatures combined or not combined with ultrasonic irradiation in specially formulated sporicidal compositions. The latter are based upon active combinations of glutaraldehyde with nonionic surfactants such as ethoxylates or isomeric linear alcohols ($C_{11}$ to $C_{15}$) or anionic alkyl aryl sulfonates.

Through a proper choice of temperatures, acoustic energy density and chemical composition the method object of the present invention enables reducing from hours to minutes the time requirements for surface disinfection or sterilization of heat sensitive materials.

Low temperature surface sterilization in liquid phase has been limited in the past to the use of two chemosterilizer agents: formaldehyde and alkaline glutaraldehyde solutions. This limited choice indeed contrasts with the large number of chemical bactericides available (Quarternary Ammonium compounds, chlorine containing compounds, Iodophores, Ampheteric compounds, etc.) when one does not require sporicidal action.

Formaldehyde is one of the oldest chemosterilizers empoloyed for the destruction of spores, and, although 1% to 2% solutions have been used, a relatively long period of time (up to 20 hours) is required to destroy *Bacillus subtilis* var. niger spores. A somewhat shorter time is needed if one uses higher concentrations of formaldehyde (around 8 per cent) in isopropyl alcohol. This solution, called Formalin has several drawbacks. The irritating fumes of formaldehyde limit its usefulness, and its toxicity for tissue requires that disinfected materials be thoroughly rinsed with sterile water before use.

Alkalanized glutaraldehyde solutions known commercially under the trade name CIDEX are the only widely used for practical applications today. They consist of a 2% aqueous glutaraldehyde solution buffered by suitable alkalinating agents (generally 0.3% sodium bicarbonate) to pH of 7.5 to 8.5. In the acid state at room temperature the glutaraldehyde solution is stable for long periods of time when stored in a closed container. However, when rendered alkaline, the glutaraldehyde gradually undergoes polymerization and loses its activity. Above pH 9 the polymerization proceeds very rapidly. In the 7.5 to 8.5 pH range polymerization is slower, but it is acknowledged by the manufacturer himself that sporicidal activity disappears after two weeks. (ARBROOK, Bulletin JR 8016, 1968)

Even when using a fresh solution of 2% buffered glutaraldehyde, the time needed at room temperature to achieve complete sterilization of Bacillus subtilis with the AOAC Pennycylinder method is said to be comprised between 3 and 10 hours according to spore dryness.

The impossibility to store the sporicidal solution over extended periods of time, the need to buffer each time before use and the long contact time required (several hours) to achieve sterility made us develop the method and new sporicidal composition objects of the present invention.

As hereabove stated, Alkalanized Glutaraldehyde has been widely used as a chemical sterilizing agent since its antimicrobial characteristics were first described in the U.S. Pat. No. 3,016,328 (1962). R. E. Pepper and E. R. Lieberman were the first to point out in the above-mentioned patent that aqueous glutaraldehyde solutions were mildly acid and in this state they stressed that they did not exhibit sporicidal characteristics. Only when the solution was buffered by suitable alkalinating agents to a pH of 7.5 to 8.5, did the solution become antimicrobially active. (see American Journal of Hospital Pharmacy 20: 458–465, Sept. 1963). This point was emphasized in the U.S. Pat. No. 3,016,328 (1962) which stated (page 1, column 2, line 34) that the invention resided in the discovery that a saturated dialdehyde containing 2 to 6 carbon does, in fact, have sporicidal activity when it is combined with a lower alkanol and an alkalinating agent.

More recently G. Sierra in Canada (Can. Pat. No. 865,913, March 1971) showed that the conclusions of R. E. Pepper and E. R. Lieberman were only valid in the temperature range (22°–23°C) indicated by these authors in their U.S. patent. The Sierra's Canadian patent indicates that strong sporicidal activity is exhibited by acid non-buffered non-alkalinized glutaraldehyde solutions when operating at temperatures higher (generally around 45°C) than those mentioned in R. E. Pepper's patent. This observation was confirmed in our own experiments. Moreover, we found, and this is one of the objects of the present invention, that with the proper combination of acid glutaraldehyde with certain nonionic or anionic surfactants at temperatures greater than 15°C but specially above 45°C higher sporicidal activities than those mentioned in G. Sierra's patent can be achieved.

An increase in bactericidal and sporicidal activity through the combined use of glutaraldehyde (both acid and alkaline) with surfactants had been previously disclosed by A. A. Stonehill in U.S. Pat. No. 3,282,775 (Nov. 1966). This inventor, however, referred only to the use of cationic agents. Several examples were given in the A. A. Stonehill's patent. They all pertained to chemical compositions using glutaraldehyde solutions with quaternary ammonium salts or cetylpyridinum chloride both of which exhibited sporicidal characteristics at room temperature within the 4 to 9 pH range.

It is an object of the present invention to show that a glutaraldehyde solution combined with nonionic or anionic agents such as ethoxylates of isomeric linear alcohols or alkyl aryl sulfonates is far more active than any other previously known sporicidal formula based upon the mixing of glutaraldehyde with cationic agents.

It is a further object of the present invention to show that the combined use of glutaraldehyde solutions with nonionic or anionic surfactants is effective over a wider pH range (1 to 9) while also working at any temperature inside the 15°C to 75°C range.

It is a further object of this invention to show that one can considerably reduce the sterilization time through simultaneous sonic or ultrasonic irradiation of the sporicidal compositions based upon a mixture of glutaraldehyde with nonionic or anionic surfactants.

To aid in the understanding of our invention we shall briefly review the various physical or chemical mechanisms which play a role in the strong sporicidal effects observed in the method object of the present invention.

A few bacteria have evolved a highly effective mechanism for ensuring their survival; they exhibit an elementary form of differentiation in which, under certain conditions, the relatively sensitive vegetative form of the organism can give rise to a resistant dormant form, called a spore. Bacterial spores are much more resistant to adverse effects of heat, radiation and chemicals than their corresponding vegetative cells. The resistance of spores differs within the microbial population and species variation is common. Among the spores which were used to evaluate the methods object of the present invention we shall mention *Bacillus subtilis*, *Bacillus stearothermopilus*, *Bacillus pumilus*, *Clostridium sporogenes* and *Clostridium tetani*.

A bacterial spore is typically about one micro diameter and consists essentially of a small cell, often called the core or spore protoplast, surrounded by a number of specialized layers. The principal layers are the thick cortex and the multilayered coats and, around spores of certain species, a further loose and thin layer called exosporium.

At the moment it is believed (C. S. Phillips, Bact. Rev. 1962) that alkylating agents such as ethylene oxide, propiolactone, formaldehyde, glutaraldehyde as well as other aldehydes attack the sulfhydryl (—SH), hydroxyl (—OH), amino (—NH$_2$) and carboxy

groups present in spore cell proteins. More recently T. J. Munton and A. D. Russell (J. Appl. Bact., 1970) stated that the chemical sites for glutaraldehyde action could involve —NH$_2$ groups, including cross linking reactions between these groups (D. Hopwood, Histochemie, 1968). According to these authors, however, the suggested mechanism does not exclude sites of action with other chemical groups.

T. J. Munton and A. D. Russell (J. Appl. Bact, 1970) also showed that the uptake of acid glutaraldehyde and alkaline glutaraldehyde (sodium bicarbonate buffer) is similar and that both are of the Langmuirian type. This was demonstrated with *E. Coli* and *Bacillus megatorium*. In other words as more sites of the bacterial cell or spores are filled, glutaraldehyde molecules find increasing difficulty in attaching themselves to the cell or spore. In the methods object of the present invention it is believed that the nonionic linear alcohol ethoxylates decrease the surface tension and increase the wettability at the spore/liquid interface in such a manner that they promote a faster absorbtion rate of glutaraldehyde molecules. This could also be the result of the entraping at the spore/liquid interface of a higher concentration of glutaraldehyde molecules. Said phenomenom being increased in a logarithmic manner with temperature inside the 15°C – 75°C range. Although of a lower magnitude the same increased rate of absorbtion at the spore/liquid interface is observed with anionic alkyl aryl sulfonates mixed with nonionic polyoxethylene alcohol ethers.

When speaking of absorbtion rates, one must point out that the increased wettability observed with the sporicidal molecules could be due not only to an increase at the external spore interface but also to a faster penetration inside the internal spore interfaces, i.e. across cortex layers, cortex or plasma membrane.

If using one of the sporicidal compositions object of the present invention in combination with ultrasonic irradiation extremely high killing rates are observed. This indeed could be explained in the following manner. As well known, the major component of a spore cortex layer is a polymer called murein (or peptidoglycan). Murein is present, in lesser amounts, in the walls of all bacteria. It is a large, cross-linked, net-like molecule exhibiting several unusual features. This polymer is acidic, and in spores may exist as a layer tightly contracted by some positively charged molecules. One recent theory to account for the extreme heat resistance of spores supposes that contractile pressure exerted by this structure may squeeze the central core sufficiently to maintain it in a state so dry as to confer heat resistance. Ultrasonic irradiation is one of the most efficient techniques (KY Sergeeva, Sov. Phys. Acoust., March 1966) to shake up polymer lattices and produce a fast depolymerization. This technique is said to be quite efficient over a wide frequency range both at low (G. Schmid et al., Kolloid L, 1951) and high frequency (M. A. K. Mostafa, J. Polym. Sci. 1958). It is therefore understandable that murein depolymerization or a partial destruction of the tight cross-linked lattice would enable the aldehyde groups to penetrate and combine faster with the active spore sites. Nonionic and anionic surfactants will indeed accelerate the penetration through the loosened polymer lattice. High intensity ultrasonic energy could also play an important role through other secondary but important mechanisms.

The proteinaceous outer coats of spores contain a disulphide-rich protein with some properties close to those of keratins. Since keratin-like proteins are typically strong, inert towards chemical reagents and resistant to enzymes they constitute an ideal protective barrier for spores. High intensity ultrasonics, however, could physically degrade keratin (J. H. Bradbury, Nature, 1960) and thus promote a faster penetration of active glutaraldehyde molecules.

Two more components characteristic of spores are high levels of calcium (often 2 per cent of the spore's dry weight) and dipicolinic acid (DPA) which may account for over 10 per cent of a spore's dry weight. Under acoustic turbulence ions exchange (Ca depletion) can take place while the heterocyclic DPA molecule could also be broken (I. E. Elpiner and A. V. Sokolskaya, Sov. Phys. Acoust. March 1963). In short, ultrasonic energy could either accelerate the physical diffusion of molecules or active radicals to reaction sites inside the spores, produce chemical bonds breakages of critical spores components (including sites modification) or both. It could also, specially with alkaline glutaraldehyde, depolymerize some of the glutaraldehyde in solution. This could be of particular significance when one remembers that alkalinized glutaraldehyde gradually loses its activity when polymerization progresses. (A. A. Stonehill et al., Am. Journ. Hosp. Phar. 1963).

Although the synergistic sporicidal effect due to a combination of moderate heat, glutaraldehyde solution and high intensity ultrasonics has been described already in G. Sierra's patent (Canadian patent application No. 098,416, 1971), the present invention shows that an addition of nonionic or anionic surfactants to the glutaraldehyde solution leads in all cases to a substantial increase in bacteria, virus or spore killing rate.

Having described our sterilization method and the sporicidal compositions to be used with it, we shall now give several examples to further illustrate the invention. They are given primarily for the purposes of illustration and should not be construed as limiting the invention to the details given.

EXAMPLES

A novel aqueous bactericidal, virucidal and sporicidal composition of the present invention is prepared with 2 percent glutaraldehyde (Union Carbide grade) and 0.2% of a nonionic surface active agent (TERGITOL 15-S-12) made by Union Carbide which is a mixture of ethoxylates of isomeric linear alcohols. The linear alkyl hydrophobic portion of the surfactant being a mixture of $C_{11}$ to $C_{15}$ linear chains. The hydrophylic portion being a polyoxyethylene chain (9 to 13 oxyethylene groups) randomly attached to the linear aliphatic chain through an ether linkage as shown in the following formula:

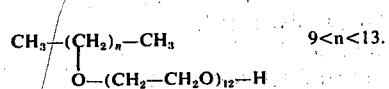

$$CH_3-(CH_2)_n-CH_3 \quad 9<n<13.$$
$$O-(CH_2-CH_2O)_{12}-H$$

The nonionic surfactant used in the formulation object of the present invention (TERGITOL 15-S-12) made by Union Carbide had the following characteristics: Molecular weight 728, Cloud point (1% aqueous solution) 90°C, Pour point 17°C, 100% solubility in water at 25°C, Apparent specific gravity 20/20°C: 1.023, density 8.49 lb/gal at 30°C, viscosity 48 CKS at 40°C, flash point 460°F. (ASTM method D 92).

The anionic surfactant blend with nonionic polyoxyethylene alcohol ethers used in the second formulation object of the present invention had the following characteristics: Specific gravity 1.02, density 8.5 lb/gal, clear liquid soluble in hot or cold water, pH comprised between 6 and 8, freezing point −10°C.

The Union Carbide grade of glutaraldehyde concentrate which was used to prepare the 2% solution used in our tests had the following characteristics: Specific gravity 1.058 to 1.065 at 20°C, glutaraldehyde concentration 24.5 to 25.5 per cent by weight, pH 2.7 to 3.7 at 25°C, Acidity 0.2 per cent by weight, maximum, calculated as acetic acid, Iron content less than 3 ppm, heavy metals content less than 2 ppm, color 125 platinum-cobalt maximum.

The spores against which the solutions have been tested were vacuum dried strains of *Clostridium Sporogenes* (ATCC 7955), *Bacillus globigii*, *Bacillus pumilus*, *Bacillus stearothermophilus* and *Bacillus Subtilis*.

The latter showed the greater resistance to the sporicidal composition and for the sake of clarity we shall restrict ourselves to the presentation of data pertaining to this microorganism.

Tests were conducted in specially designed ultrasonic stainless steel tanks (Wave Energy Systems series CTG 160) with a 2 gallon capacity. One gallon of spores suspension was used in each test. The acoustic output in liquid phase could vary from 10 to 30 watts per liter of spores suspension. The experimental irradiation frequency was either 10 kHz or 27 kHz (± 1 kHz). At high frequency (850 kHz, 20 watts/liter and 5 watts/cc) the spore solution was contained in a 2 gal glass beaker which was placed in a water filled container fitted at the bottom with a submersible transducer (glazed cobalt lead zirconate titanate). During all experiments the temperature was thermostatically controlled at ± 1°C.

As previously stated, spores of Bacillus subtilis (ATCC 6051) were used in all the reported experiments. The preparation of clean spores was accomplished with the G. Sierra and A. Bowman technique (Journ. Appl. Microbiology, 17: 372–378, 1969). The spores were pasteurized (80°C, 15 min) and stored at 4°C as concentrated suspensions in deionized water and used within one week. The standardization of the spore suspensions was carried out as described by G. Sierra (Can. Journ. Microbiology, 13: 489–501, 1967).

Glutaraldehyde and glutaraldehyde/surfactant solutions were freshly prepared in deionized water for each experiment. Concentrated stock solution of the buffers or sodium bicarbonate were added separately to pasteurized spore suspensions. The pH values reported here are those of a complete system after all additions and were read with a Beckman Zeromatic II pH meter, the calibration of which was checked before each assay was run. Stirring was continuous, and the pH was read after allowing the electrode potential to stabilize.

To recover spore survivors efficiently (especially in the lower dilutions) the effects of glutaraldehyde carryover into the viable count plates was counteracted by quenching the glutaraldehyde with sodium bisulphite before plating. After the desired treatment samples of 0.5 ml were taken to determine the numbers of surviving spores. Each sample was diluted immediately into 4.5 ml of 1% sodium bisulphite + 0.1% peptone solution and allowed to stand for 10 min, after which further serial dilutions were made in 0.5% sodium bisulphite + 0.1% peptone solution. Colony counts from 0.1 ml amounts of appropriate dilutions were made on 0.1% starch-nutrient agar; duplicate plates were incubated at 30°C for 3 days. The bisulphite treatment was found neither to potentiate glutaraldehyde induced spore inactivation nor cause detectable direct inactivation of intact spores.

In a few instances it could be of interest to use as a diluent not only filtered deionized water but a lower alkanol such as methanol, ethanol, isopropanol and the like. A mixture of both could also be used and in Table IV we give the results of a test conducted with a composition comprising 60% isopropyl alcohol with 37.8% water, 2% glutaraldehyde and 0.2% nonionic surfactant. Tables I to V show some typical results of our experiments conducted with suspensions of Bacillus Subtilis (ATCC 6051) under variable conditions (glutaraldehyde concentration, different surfactants, varying temperature and pH).

TABLE I

Various concentration of glutaraldehyde
Initial spores count 10⁷/ml. temperature 55°C.
Ultrasonic field: Frequency 27 kHz, Intensity 20 watts/liter.
pH 5.

| Glutaraldehyde Concentration | Minimum time in minutes for 100% kill |
|---|---|
| 0.1% | 20 with ultrasound |
| 2 | 15 with ultrasound |
| 5 | 15 with ultrasound |
| 0.1 | 40 no ultrasound |
| 2 | 30 no ultrasound |
| 5 | 30 no ultrasound |
| 2 | 10 with ultrasound and nonionic surfactant (0.2%) |

TABLE I-continued

Various concentration of glutaraldehyde
Initial spores count $10^7$/ml. temperature 55°C.
Ultrasonic field: Frequency 27 kHz, Intensity 20 watts/liter
pH 5.

| Glutaraldehyde Concentration | Minimum time in minutes for 100% kill |
|---|---|
| 2 | 20 no ultrasound but with nonionic surfactant (0.2%) |

TABLE II

Various concentration of different synergistic surfactants
Initial spores count $10^7$/ml temperature 55°C
Ultrasonic field: Frequency 27 kHz, Intensity 20 watts/liter
Glutaraldehyde concentration: 2%
pH 5.

| Type of surfactant | Surfactant concentration | Minimum time in min. for 100% kill |
|---|---|---|
| nonionic* | 0.02% | 11 |
| nonionic | 0.2 | 10 |
| nonionic | 1 | 10 |
| anionic** | 0.02 | 12 |
| anionic | 0.2 | 11 |
| anionic | 1 | 11 |
| cationic*** | 0.2 | 15 |
| no surfactant (glutaraldehyde alone) | | 15 |

*ethoxylates of isomeric linear alcohols
**alkyl aryl sulfonate mixed with polyoxethylene alcohol ethers
***cetylpyridinium chloride

TABLE III

Activity at various temperatures
Initial spores count $10^7$/ml
Ultrasonic field: Frequency 27 kHz, Intensity 20 watts/liter
Glutaraldehyde concentration 2% - Nonionic surfactant concentration: 0.2%
pH 5

| Temperature | Minimum time in min. for 100% kill |
|---|---|
| 15°C | 120 |
| 25°C | 100 |
| 45°C | 60 |
| 55°C | 10 |
| 65°C | 5 |

TABLE IV

Activity at various pH 5
Initial spores count $10^7$/ml
Ultrasonic field: Frequency 27 kHz, Intensity 20 watts/liter
Glutaraldehyde concentration 2%, Nonionic surfactant concentration: 0.2%
Temperature: 55°C

| Diluent | pH | | Minimum time in min. for 100% kill |
|---|---|---|---|
| Deionized water | 2.5 | | 11 |
| Deionized water | 5 | | 10 |
| Deionized water | 6 | | 10 |
| Deionized water | 8 | (with buffer) | 10 |
| Deionized water | 10 | (with buffer) | 12 |
| Water and isopropyl alcohol (66%) | 6.5 | | 10 |

TABLE V

Activity at various ultrasonic frequencies and intensities
Initial spores count $10^7$/ml.
Glutaraldehyde concentration 2%, nonionic or anionic surfactant concentration: 0.2%
Temperature: 55°C
pH 6

| Type of Surfactant | Ultrasonic Frequency in kHz | Energy density | Minimum time in min. for 100% kill |
|---|---|---|---|
| nonionic | 27 | 20 watts/liter | 10 |
| nonionic | 27 | 30 watts/liter | 6 |
| nonionic | 27 | 1 watt/liter | 18 |
| nonionic | 10 | 20 watts/liter | 10 |
| nonionic | 10 | 30 watts/liter | 6 |
| nonionic | 850 | 20 watts/liter | 12 |

TABLE V-continued

Activity at various ultrasonic frequencies and intensities
Initial spores count $10^7$/ml.
Glutaraldehyde concentration 2%, nonionic or anionic surfactant concentration: 0.2%
Temperature: 55°C
pH 6

| Type of Surfactant | Ultrasonic Frequency in kHz | Energy density | Minimum time in min. for 100% kill |
|---|---|---|---|
| nonionic | 850 | 5 watts/cc | 4 |
| anionic | 27 | 20 watts/liter | 12 |

The data contained in these tables clearly show the synergistic effects obtained with two types of sporicidal compositions based upon nonionic and anionic surfactants dissolved in glutaraldehyde. They also show that the teachings of the invention may be practiced within the following parameters:

Glutaraldehyde concentration: from about 0.1% to about 5%.

Nonionic, or anionic blend with nonionic surfactant: from about 0.1% to about 1%.

Acoustic field frequency: from about 10 kHz to about 850 kHz.

Acoustic field energy density: from about 1 watt/liter to about 5 watt/cc.

Diluent: water or lower alkanol.

Temperature: above 15°C pH range: 2 to 10

Although several specific examples of the inventive concept have been described for purposes of illustration, the invention should not be construed as limited thereby nor to the specific features mentioned therein except as the same may be included in the claims appended hereto. It is also understood that changes, modifications, and variations may be made without departing from the spirit and scope of the present invention.

The embodiments of the invention in which an exclusive property or privilege is claimed are defined as follows:

1. A sterilization and disinfectant composition comprising from about 0.1% to about 5% of glutaraldehyde and from about 0.01 to 1% of a nonionic surface active agent which is an ethoxylate of isomeric linear alcohols having the following formula:

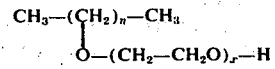

wherein $n$ is 9 to 13 and $x$ is 9 to 13.

2. The disinfecting and sterilizing composition of claim 1 also containing a sufficient quantity of a lower alkanol to make a final alcoholic concentration of from about 60% to about 75%.

3. A sporicidal composition having a pH of 6.5 consisting essentially of 2% by weight glutaraldehyde, 1% by weight nonionic surface active agent and water.

* * * * *